US010588999B2

(12) United States Patent
Kalkhoran et al.

(10) Patent No.: US 10,588,999 B2
(45) Date of Patent: Mar. 17, 2020

(54) MESOPOROUS SURFACE FOR ENHANCED BONE INTEGRATION

(71) Applicants: Nader Montazemezam Kalkhoran, Tewksbury, MA (US); Eric Tobin, North Andover, MA (US); Jason Burns, Cambridge, MA (US)

(72) Inventors: Nader Montazemezam Kalkhoran, Tewksbury, MA (US); Eric Tobin, North Andover, MA (US); Jason Burns, Cambridge, MA (US)

(73) Assignee: N2 BIOMEDICAL LLC, Bedford, MA (US)

( * ) Notice: Subject to any disclaimer, the term of this patent is extended or adjusted under 35 U.S.C. 154(b) by 22 days.

(21) Appl. No.: 15/790,384

(22) Filed: Oct. 23, 2017

(65) Prior Publication Data

US 2018/0110898 A1 Apr. 26, 2018

Related U.S. Application Data

(60) Provisional application No. 62/411,853, filed on Oct. 24, 2016.

(51) Int. Cl.
| | |
|---|---|
| *A61L 27/10* | (2006.01) |
| *A61L 27/06* | (2006.01) |
| *A61L 27/54* | (2006.01) |
| *A61L 27/30* | (2006.01) |
| *A61L 27/56* | (2006.01) |

(Continued)

(52) U.S. Cl.
CPC ............... *A61L 27/10* (2013.01); *A61L 27/06* (2013.01); *A61L 27/306* (2013.01); *A61L 27/54* (2013.01); *A61L 27/56* (2013.01); *A61F 2002/0086* (2013.01); *A61K 47/02* (2013.01); *A61L 2400/12* (2013.01); *A61L 2400/18* (2013.01); *A61L 2430/02* (2013.01)

(58) Field of Classification Search
None
See application file for complete search history.

(56) References Cited

U.S. PATENT DOCUMENTS

| 10,022,232 B2* | 7/2018 | Mandanici | ........... A61C 8/0013 |
|---|---|---|---|
| 2006/0173497 A1* | 8/2006 | Mech | ..................... A61N 1/372 |
| | | | 607/2 |

(Continued)

OTHER PUBLICATIONS

Huang et al. Preparation, characterization and in vitro response of bioactive coatings on polyether ether ketone. Electrocimica Acta Vo.. 199. May 2016. pp. 116-125 (Year: 2016).*

(Continued)

*Primary Examiner* — Cachet I Proctor
(74) *Attorney, Agent, or Firm* — Hunter Clark PLLC

(57) ABSTRACT

Techniques for creating a mesoporous surface for enhanced bone integration are provided. An example of a method for generating a mesoporous surface on a substrate includes depositing a layer of titanium on an area of the substrate to generate a nano-textured surface, and anodizing the layer of titanium on the area of the substrate to generate the mesoporous surface. The method may also include incorporating pharmaceutical, biological, or molecular additives into the mesoporous surface intended to further enhance performance of the substrate via enhanced osseoconduction, osseoinduction, or antimicrobial/anti-infective properties.

11 Claims, 5 Drawing Sheets

(51) Int. Cl.
  *A61K 47/02*  (2006.01)
  *A61F 2/00*  (2006.01)

(56) References Cited

U.S. PATENT DOCUMENTS

| | | | | |
|---|---|---|---|---|
| 2006/0175653 A1* | 8/2006 | Joo | B82Y 10/00 | 257/314 |
| 2006/0210494 A1* | 9/2006 | Rabiei | A61C 8/0012 | 424/57 |
| 2007/0096281 A1* | 5/2007 | Greenberg | A61N 1/375 | 257/682 |
| 2008/0039768 A1* | 2/2008 | Francis | A61M 5/14276 | 604/8 |
| 2009/0276053 A1* | 11/2009 | Brown | A61F 2/2846 | 623/18.11 |
| 2010/0016985 A1* | 1/2010 | Rabiei | A61K 6/08 | 623/23.6 |
| 2010/0109205 A1* | 5/2010 | Fletcher | B82Y 10/00 | 264/447 |

OTHER PUBLICATIONS

Park et al. Mesoporous TiO implants for loading high dosage of antibacterial agent. Applied Surface Science. vol. 303. Jun. 2014. pp. 140-146 (Year: 2014).*

Harmankaya et al. Raloxifene and alendronate containing thin mesoporous titanium oxide films improve implant fixation to bone. Acta Biomaterialia. vol. 9. Issue 6. Jun. 2013. pp. 7064-7073. (Year: 2013).*

* cited by examiner

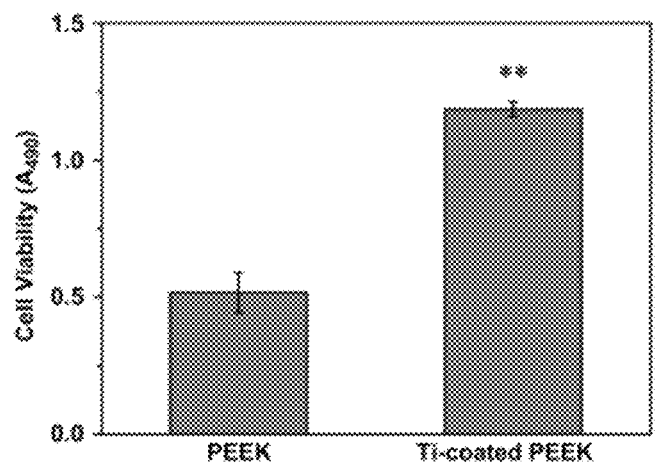
FIG. 2A
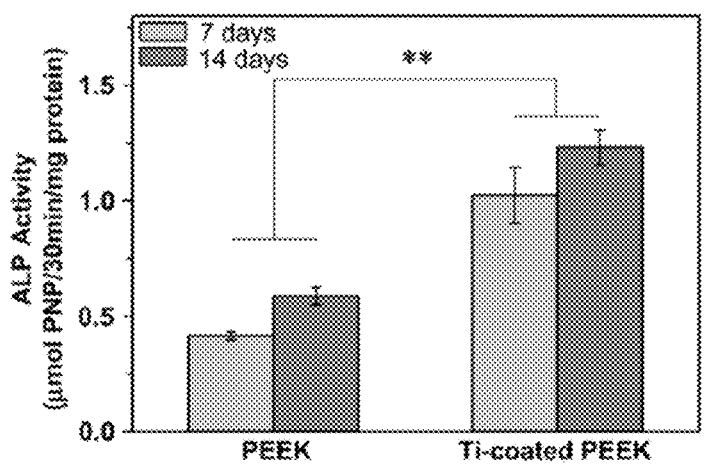
FIG. 2B
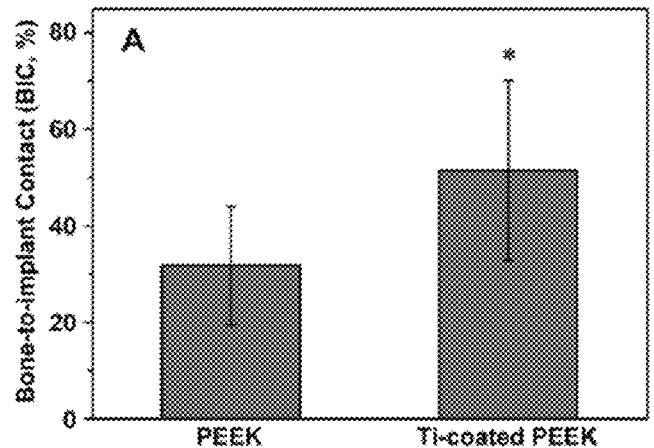
Prior Art        FIG. 2C

MESOPOROUS SURFACE FOR ENHANCED BONE INTEGRATION

CROSS-REFERENCE TO RELATED APPLICATIONS

This application claims the benefit of U.S. Provisional Application No. 62/411,853, filed Oct. 24, 2016, entitled "MESOPOROUS SURFACE FOR ENHANCED BONE INTEGRATION," the entire contents of which is hereby incorporated herein by reference.

BACKGROUND

Bio-implants often fail due to effects of bacterial diseases and/or insufficient integration of the medical device into the surrounding tissue. Typical medicinal and surgical treatment options are often inadequate with regard to preventing failure of these devices. For example, the use of polyetheretherketone (PEEK) is increasing for bio-implant medical device applications. While the material's bioinertness is a key advantage, this property also results in less rapid and incomplete integration with host tissue, particularly in spinal and orthopedic applications. Thus, there is a need for bioactive additives and coatings to improve the function of PEEK in current bio-implant applications and potentially expand its use into new areas.

SUMMARY

An example of a method for generating a mesoporous surface on a substrate according to the disclosure includes depositing a layer of titanium on an area of the substrate to generate a nano-textured surface, and anodizing the layer of titanium on the area of the substrate to generate the mesoporous surface.

Implementation of such a method may include one or more of the following features. The substrate may be a non-conductive material. The substrate may be a polyetheretherketone (PEEK) material. The area of the substrate may be grit-blasted to generate a macro-textured surface prior to depositing the layer of titanium. Grit-blasting the area of the substrate may include air-blasting the area with 50-100 μm in diameter micro-beads of $SiO_2$ or $Al_2O_3$. Pharmaceutical, biological, or molecular additives may be incorporated into the mesoporous surface intended to further enhance performance of the substrate via enhanced osseoconduction, osseoinduction, or antimicrobial/anti-infective properties. A layer of titanium may be deposited on the area of the substrate with an ion beam assisted deposition (IBAD) process. The IBAD process may utilize an ion beam energy between 50 eV and 5000 eV. The layer of titanium may be between 2 μm to 4 μm thick. Anodizing the layer of titanium on the area of the substrate may include an electrochemical oxidation process in a hydrofluoric (HF) acid-based solution. Anodizing the layer of titanium on the area of the substrate may include an electrochemical oxidation process in an ammonium fluoride ($NH_4F$) acid-based solution. Anodizing the layer of titanium on the area of the substrate may include an electrochemical oxidation process in a solution of nitric acid, hydrochloric acid, acetic acid, trichloroacetic acid, phosphoric acid, sulfuric acid, potassium hydroxide, sodium hydroxide, or combinations thereof. The mesoporous surface may include pore sizes of between 1-50 nanometers in a lateral dimension and between 10-500 nanometers in depth.

An example of a system for generating a mesoporous surface on a substrate according to the disclosure may include a means for depositing a layer of titanium on an area of the substrate to generate a nano-textured surface, and a means for anodizing the layer of titanium on the area of the substrate to generate the mesoporous surface. The substrate comprises a polyetheretherketone (PEEK) material. The system may include means for grit-blasting the area of the substrate to generate a macro-textured surface prior to depositing the layer of titanium. The means for grit-blasting the area of the substrate may include means for air-blasting the area with 50-100 μm in diameter micro-beads of $SiO_2$ or $Al_2O_3$. The system may include a means for incorporating pharmaceutical, biological, or molecular additives into the mesoporous surface intended to further enhance performance of the substrate via enhanced osseoconduction, osseoinduction, or antimicrobial/anti-infective properties. Depositing the layer of titanium on the area of the substrate may be performed with an ion beam assisted deposition (IBAD) means. The IBAD means may utilize an ion beam energy between 50 eV and 5000 eV. The layer of titanium may be between 2 μm to 4 μm thick. Anodizing the layer of titanium on the area of the substrate may include an electrochemical oxidation process in a hydrofluoric (HF) or an ammonium fluoride ($NH_4F$) acid-based solution.

An example of a biomedical implant according to the disclosure includes a substrate, and a mesoporous surface on an area of the substrate, such that the mesoporous surface includes an anodized layer of titanium on the area of the substrate, the mesoporous surface being generated by depositing a layer of titanium on the substrate to generate a nano-textured surface, and anodizing the layer of titanium on the area of the substrate to generate the anodized layer of titanium.

Items and/or techniques described herein may provide one or more of the following capabilities, as well as other capabilities not mentioned. A highly-adherent $Ti/TiO_2$ coating structure may be deposited on a non-conductive substrate. In an example, the substrate may comprise a polyetheretherketone (PEEK) substrate such as a PEEK medical device. An area of a PEEK substrate may be grit blasted to form a macro textured surface. An ion beam assisted deposition (IBAD) process may be used to deposit a layer of titanium on the area to enhance favorable biological reactivity such as osseointegration and/or to generate a nano-textured surface. The titanium layer may be anodized to create a colored surface and/or generate a mesoporous surface. Further, the nanometer-scale pores may be filled with pharmaceutical, biological, or other molecular agents to further enhance device properties. Integration of a treated PEEK medical device with host tissues may be accelerated. For example, osteoblast formation and osseointegration may be enhanced. Also, the coating structure may provide antimicrobial properties via the surface morphology, photocatalytic effects of the titanium oxide surface, or incorporation of antimicrobial compounds into the porous structure. The mechanical properties of the PEEK medical device may remain intact. While the examples described herein refer to PEEK devices, the invention is not so limited. The processes may be used to create mesoporous surfaces on other polymers and metals, such as substrates composed at least in part of a thermoplastic, a stainless steel alloy, titanium, cobalt chromium, a ceramic (e.g., alumina, zirconia, aluminum oxynitride, titania, etc.), and/or combinations thereof. Other capabilities may be provided and not every implementation according to the disclosure must provide any, let alone all, of the capabilities discussed. Further, it may be possible for an effect noted above to be achieved by means other than that noted, and a noted item/technique may not necessarily yield the noted effect.

BRIEF DESCRIPTION OF THE DRAWINGS

FIGS. 2A-2C include graphs comparing properties of PEEK to Ti-coated PEEK.

DETAILED DESCRIPTION

Techniques are discussed herein for generating a mesoporous surface on non-conductive substrates such as PEEK bio-implants, and more specifically for using ion beam assisted deposition (IBAD) to deposit a highly adherent micro- and/or nano-structured Titanium (Ti) coating. A number of approaches have been evaluated for enhancing bioactivity of PEEK medical devices, but currently available technologies have drawbacks that may limit their effectiveness or widespread application. For example, bioactive fillers such as hydroxyapatite can compromise mechanical properties of the material. Further, since PEEK is inert, it is difficult to apply sufficiently adherent bioactive coatings. The present application provides for a highly-adherent Ti/TiO2 coating structure with four engineered levels of texturing in macro, micro, nano, and meso scale to induce preferential osteoblast formation and enhance osseointegration. Three distinct surface modification techniques may be used to produce a multi-level textured structure. Low-temperature grit-blasting may be used initially to produce a macro-textured surface on PEEK substrates. An IBAD technique is then used to deposit a highly adherent micro- and nano-structured Ti coating. Finally, an anodic oxidation technique may be used to form a mesoporous bioactive TiO2 layer on the surface of the implant.

In general, the use of polyaryletherketone (PAEK) as an orthopedic biomaterial is known. PAEK consists of an aromatic backbone molecular chain interconnected by ketone and ether functional groups. The chemical structure provides stability at high temperatures, resistance to chemical and radiation damage, compatibility with many reinforcing agents, and a higher strength-to-weight ratio than many metals. The resistance of PAEK materials to degradation in the body, as well as the ability to tailor the elastic modulus via the addition of fillers and reinforcement agents, prompted interest in its usage as an orthopedic biomaterial. Following the commercial introduction of PAEK as an implant material, poly(aryl-ether-ether-ketone) (PEEK) has become a broadly used material in spinal fusion devices. The radiolucency properties of PEEK permits healing site monitoring and implant placement verification.

Figure 1:
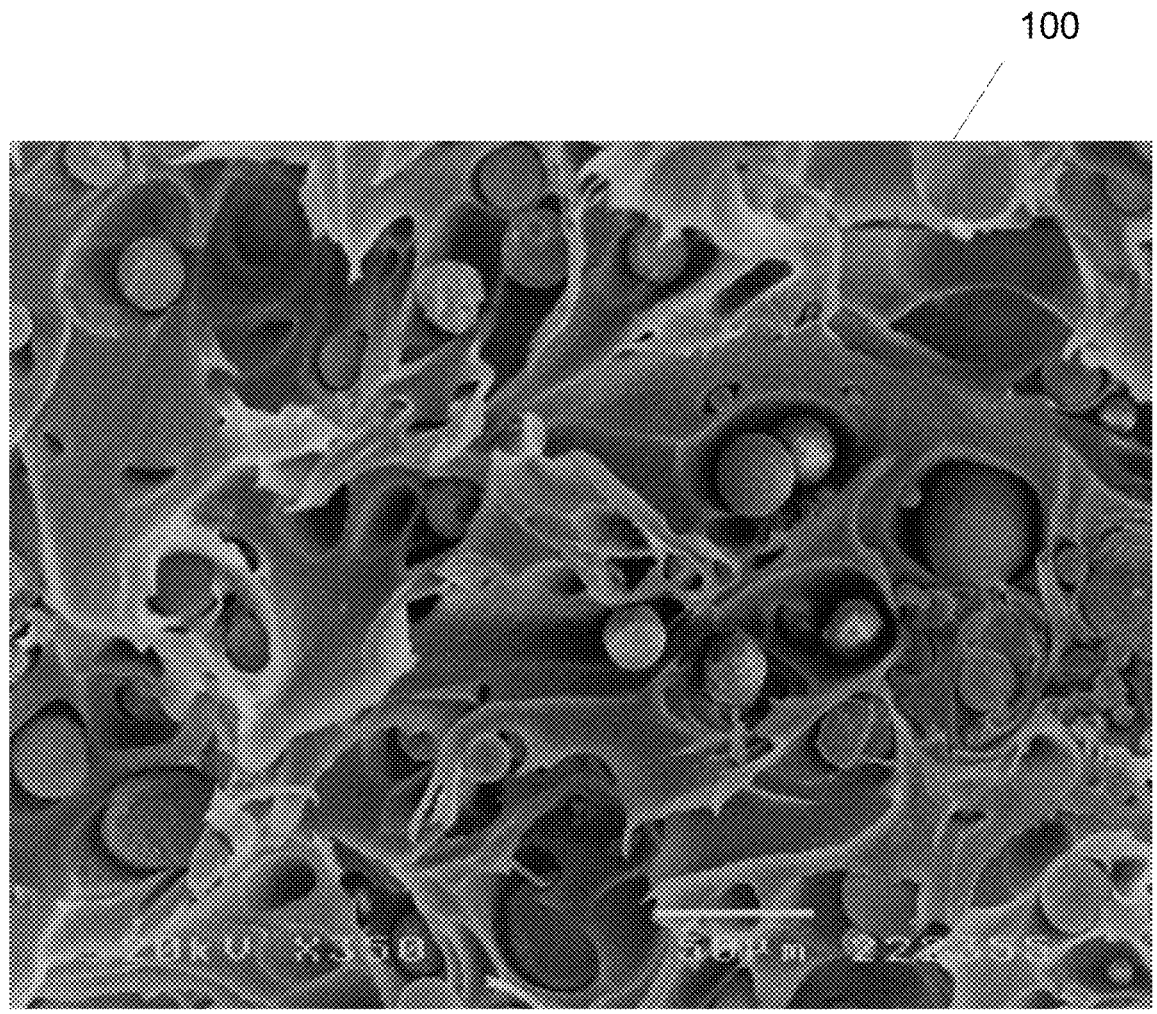
FIG. 1 is a scanning electron micrograph 100 of a fracture surface of a PEEK-10% HA composite.

PEEK is generally categorized as a bioinert, rather than bioactive, material. This has prompted interest in surface coatings and PEEK composite materials to enhance bioactivity, prompting faster and more complete osseointegration in load-bearing applications. One prior approach to enhancing bioactivity has been to fabricate PEEK-Hydroxyapatite (PEEK-HA) composites, typically by injection molding. These attempts have sometimes resulted in enhanced bioactivity. However, the addition of HA to the PEEK material has resulted in degradation of PEEK's mechanical properties. While the additives increase the elastic modulus, they simultaneously decrease the ultimate tensile strength (UTS) of the material. In fact, PEEK loading with 40% HA has been shown to reduce the UTS by 45%. Referring to FIG. 1, a scanning electron micrograph 100 of a fracture surface of a PEEK-10% HA composite is shown. FIG. 1 depicts the debonding of the HA particles from the PEEK matrix. This decrease in strength is potentially due to the lack of affinity of calcium phosphate materials to the PEEK matrix.

Referring to FIGS. 2A-2C, graphs comparing properties of PEEK to Ti-coated PEEK are shown. As an alternative to loading PEEK with calcium phosphate or other bioactive materials, surface coatings of either calcium phosphate/HA or titanium using various deposition methods have been evaluated. In cell culture tests, for example, osteoblast cells appear to spread more actively on the Ti-coated discs compared to their uncoated counterparts. Additionally, the number of living cells on the Ti-coated discs may be more than twice that on the uncoated substrates (FIG. 2A), and there may be an increase in the alkaline phosphatase levels observed at both 7 and 14 days (FIG. 2B). In animal studies, the Ti-coated PEEK samples showed an increase in the bone-implant contact (BIC) length compared to the uncoated portion (FIG. 2C). In an example, Ti-coated PEEK may be more wettable than the uncoated material (e.g., water contact angle changed from 72 degrees uncoated to 54 degrees coated). This enhanced bioactivity may be partially a result of the increased wettability.

Conventional metallization processes (e.g., evaporation, sputter-coating, electroplating) have difficulty forming homogeneous, adherent coatings on polymers such as PEEK. Although suitably adherent coatings can be deposited in some cases for short-term environmental exposure, these techniques rarely produce coatings with sufficient long-term adhesion to withstand years of exposure to the biological environment. Additionally, although it has better temperature resistance than most polymeric materials, PEEK's melting temperature of 334° C. and glass transition temperature of about 145° C. still prohibit exposure of the material to the very high temperatures used in many thin film deposition processes. As described herein, a low temperature deposition process may provide suitable polymer/metal bonding to assure long-term adhesion. For example, ion beam assisted deposition is a means of simultaneously satisfying these requirements.

Figure 3:
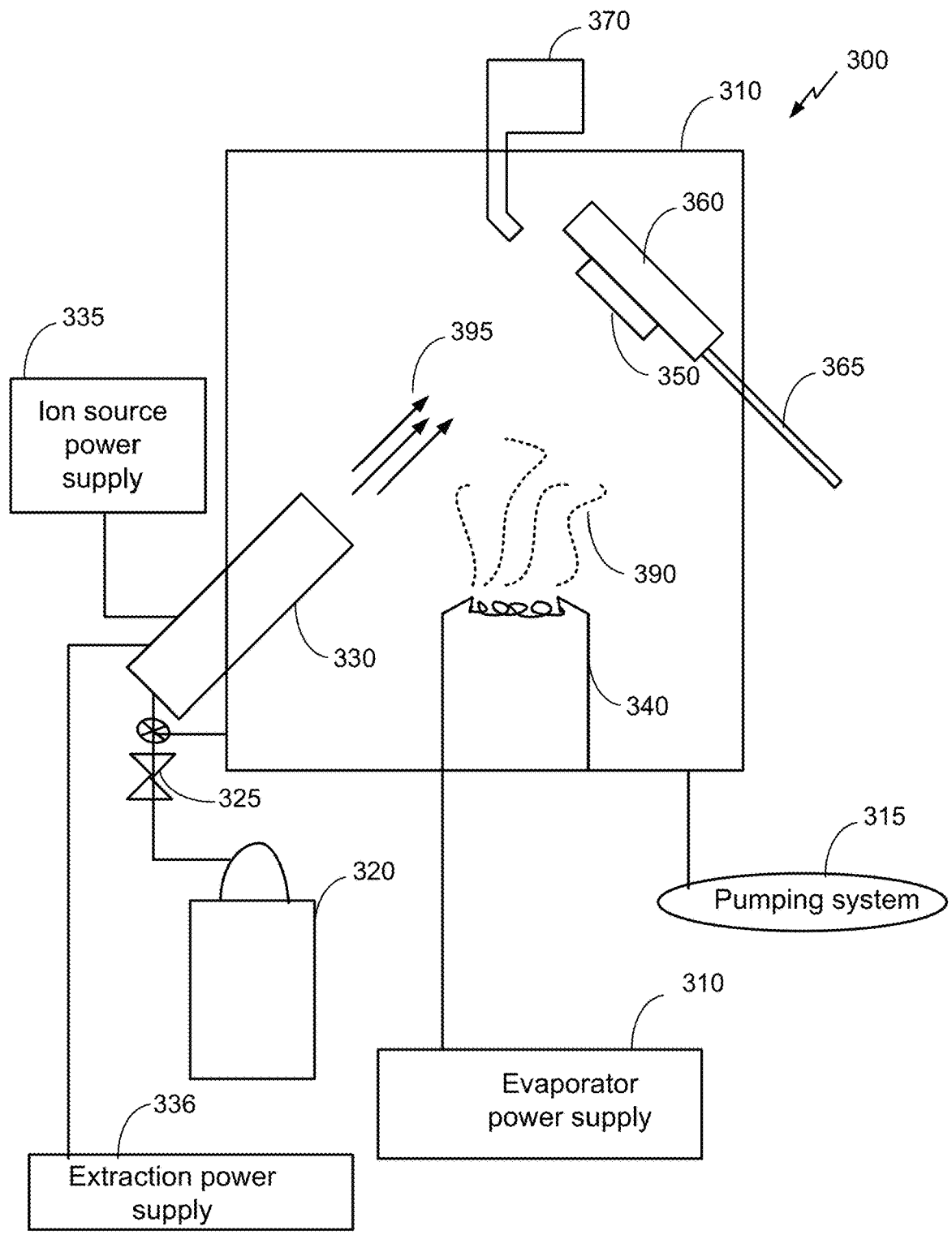
FIG. 3 is a schematic diagram of an example of a processing chamber for an ion beam assisted deposition process.

Referring to FIG. 3, a schematic diagram of an example system 300 with a processing chamber for an ion beam assisted deposition (IBAD) process is shown. The system 300 is an example and not limiting and may be altered, e.g., by having components added, removed, or rearranged. A quantity of each component in FIG. 3 is an example only and other quantities of each, or any, component could be used. Such systems are known in the art. For example, U.S. Pat. No. 5,236,509, herein incorporated by reference, describes an IBAD apparatus that is suitable for use in producing a mesoporous surface on a PEEK implant in accordance with the disclosure. The system 300 includes a processing chamber 310, a pumping system 315 and a gas supply source 320. The gas supply source 320 is coupled to a mass flow controller 325 and an ion source 330. The mass flow controller may provide gases to the processing chamber 310 at or below a flow rate of 100 standard cubic centimeters per minute (SCCM) flow rate. The gas supply source 320 is configured to supply one or more gases (e.g., Ar, Ne, Xe, He, O, N, etc.) to the ion source 330 and/or the processing chamber 310. The gas supply source 320 may be configured to supply the one or more gases as a backfill gas. The ion source may be a bucket type ion source or any other suitable ion source. A mass flow controller 325 regulates the rate of flow of the one or more gases from the gas supply source 320 to the ion source 330. An ion source power supply 335 maintains an arc discharge between the anode and the filaments and an extraction power supply 336 is configured to accelerate the ions through one or more accelerator grids of the ion source 330. The accelerated ions form an ion beam 395. The ion beam energy may be 50-5000 electron volts (eV). The extraction power supply 336 determines the ion beam energy and may determine the arrival rate of the ion beam. The ion source power supply and/or the mass flow controller may determine the arrival rate of the ion beam 395. The ion beam 395 may include one or more gas species.

An evaporator 340 also is mounted in the processing chamber 310 in operative association with the ion source 330. The evaporator 340 may be an electron beam evaporator. The evaporator 340 is designed to vaporize particular metallic evaporants (e.g., vapor plume 390) so as to dry-coat a specific substrate 350 therewith, being assisted in the dry-coating by an ion beam 395 emanating from the ion source 330. Metallic and ceramic evaporants may include Ti and its respective alloys, oxides and compounds. For example, Ti for evaporation may be 99.8% pure in 6 mm pellets, and titania may be 99.9% pure, in 3-6 mm pellets. The evaporator 340 may include one or more evaporant sources with each evaporant source configured to include one metallic evaporant. Further, the evaporator 340 may be configured to co-evaporate multiple materials and produce the vapor plume 390 including one or more materials. In this case, two or more materials may be co-deposited (i.e., deposited concurrently) onto the substrate 350. An electron beam current of the evaporator 340 determines a deposition rate for the metallic evaporants. The deposition rate of each material may be independently controlled so that each species of multiple materials may have a respective deposition rate. In this way, one or more materials may be added to the vapor plume 390 and varying deposition rates of the various materials may be provided. During co-deposition, the ratio of the multiple materials in the vapor plume 390 may be the same throughout the deposition process or may change. For example, the vapor plume 390 may include more of a particular material than the other materials and the ratio between materials may be selected and controlled as a processing parameter.

The substrate 350 is provided in the processing chamber 310 with the aid of a suitable substrate holder 360. Preferably, the substrate holder 360 is mounted for both rotational and translational motion on a shaft 365. The substrate holder 360 may be a double-planetary fixture. This type of fixture rotates its components around two parallel axes, while simultaneously translating through the treatment zone. This may allow control of and optimization of packing density and coating uniformity for the deposited film. In an embodiment, the substrate holder 360 may be configured as a heat source or heat sink for the substrate. For example, the substrate holder may include a cooling system, such as a water cooling system. The system 300 may include a thickness monitor 370 in operative association with the substrate holder 360 to monitor the thickness of the film being deposited on the substrate 350 during operation of the system 300.

In general, the IBAD process includes a number of parameters, each of which can influence the properties of the film deposited on the substrate surface. A control system including one or more computers and the corresponding software may be operably coupled to the system 300 and configured to control these parameters. Some of these parameters include evaporant deposition rate, electron beam current, arrival rate or current density of the ion beam, ion species, ion beam energy, backfill species, and backfill flow rate. Evaporant deposition rates can vary from about 0.5 Angstroms per second (Å/s) to approximately 100 Å/s. The electron beam current is controlled via a feedback loop with the thickness monitor 370 and adjusted based on the desired deposition rate. The arrival rate of the ion beam can be in a range between about 10 to about 500 microamperes per square centimeter per second ($\mu A/cm^2/sec$). The ion species may be one or more ionized noble gases, for example, Ar, Xe, Ne, He, etc. and/or one or more reactive gases, for example, O, N, etc. The ion beam energy may be 50 electron volts (eV) to about 5000 eV. The backfill species may be one or more reactive gases, for example, oxygen and/or nitrogen. The backfill flow rate may be ≤100 SCCM. Additionally, the crystal size (e.g., an average crystal size or a maximum crystal size) of the deposited film may be a function of the ion beam parameters.

In operation, the system 300 is used in the formation of a Ti/TiO2 structure on PEEK with four degrees of surface texture engineered to promote osteoblast formation and bone-ingrowth onto a PEEK device. The Ti/TiO2 structure will be used as part of a process to add surface textures on a PEEK-based devices at Macro (>100 μm), Micro (1-100 μm), and nano (1-200 nm) scales, as well as rendering a functional mesoporous (1-50 nm pores) TiO2 layer on top to improve osteoblast production and growth. The mesoporous medium not only provides a large surface area for cell attachment, but also acts as a reservoir for fluids and nutrients cells need to grow and thrive. A conventional grit-blasting approach may be used to initially produce a macro-texture on the surface of the PEEK devices. The micro- and nano-texture may be engineered by depositing a titanium layer using an IBAD process. The IBAD process combines physical vapor deposition (PVD) with ion-beam bombardment to overcome the limitations of conventional PVD processes and produce highly adherent coatings of exceptionally high quality at low deposition required for polymer-based substrates such as PEEK. IBAD enhances adhesion by a) removing surface contaminants, b) increasing atom reactivity, c) increasing nucleation density, d) increasing surface mobility of coating atoms, e) decreasing formation of interfacial voids, and f) introducing thermal energy to the surface region.

Figure 4A:
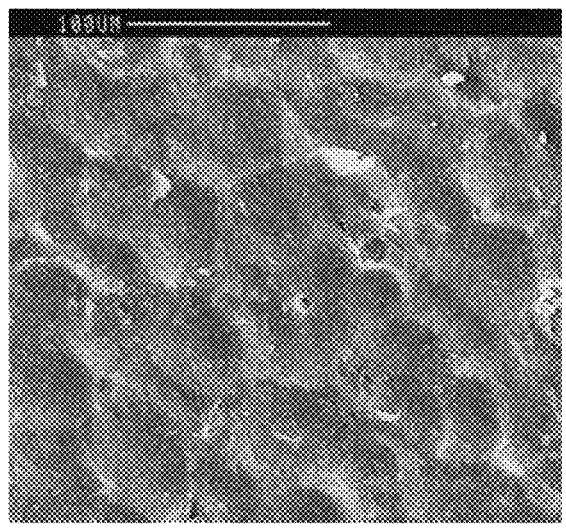
FIGS. 4A-4C are scanning electron microscope images of surface textures on a PEEK-based device.
Figure 4B:
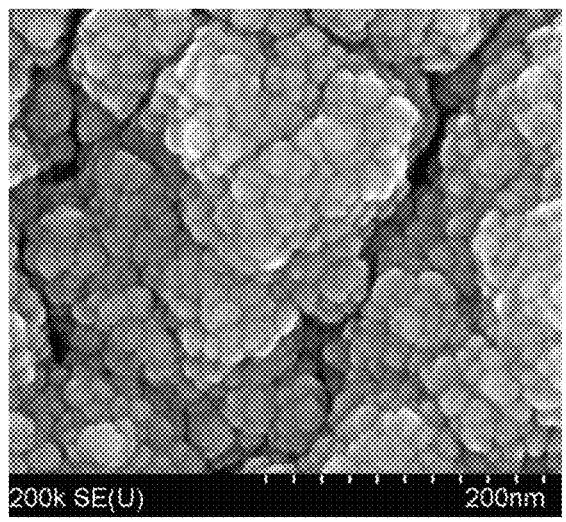
Figure 4C:
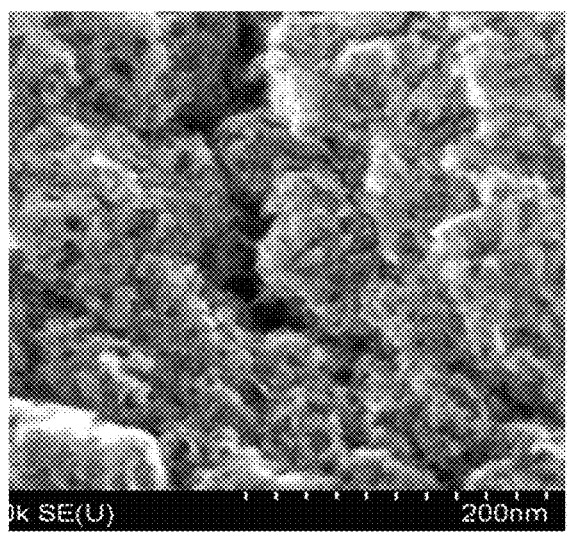

Referring to FIGS. 4A-4C, scanning electron microscope (SEM) images of surface textures on a PEEK-based device are shown. In general, controlling IBAD process parameters enables the engineering of highly adherent Ti coatings on a variety of substrates, including PEEK. FIG. 4A depicts a PEEK-based device after a grit blasting process, which results in a macro-textured PEEK surface. IBAD processes are then performed to generate surface textures both in the micro- and nano-scale range. For example, the cauliflower-like morphology in FIG. 4B results from the energy transfer from the ion beam, which causes increased nucleation density and increased surface mobility of coating atoms. High ion beam exposure breaks up crystal grains before they can grow to their natural size, yielding nano-crystallites in a microstructure formation. A fourth degree of surface texture includes the formation of a mesoporous TiO2 surface layer within the Ti nano-structured matrix using an anodization process. FIG. 4C is a SEM image of a mesoporous TiO2 top layer formed on a nano-structured Ti coating deposited by IBAD on PEEK substrates.

Figure 5:
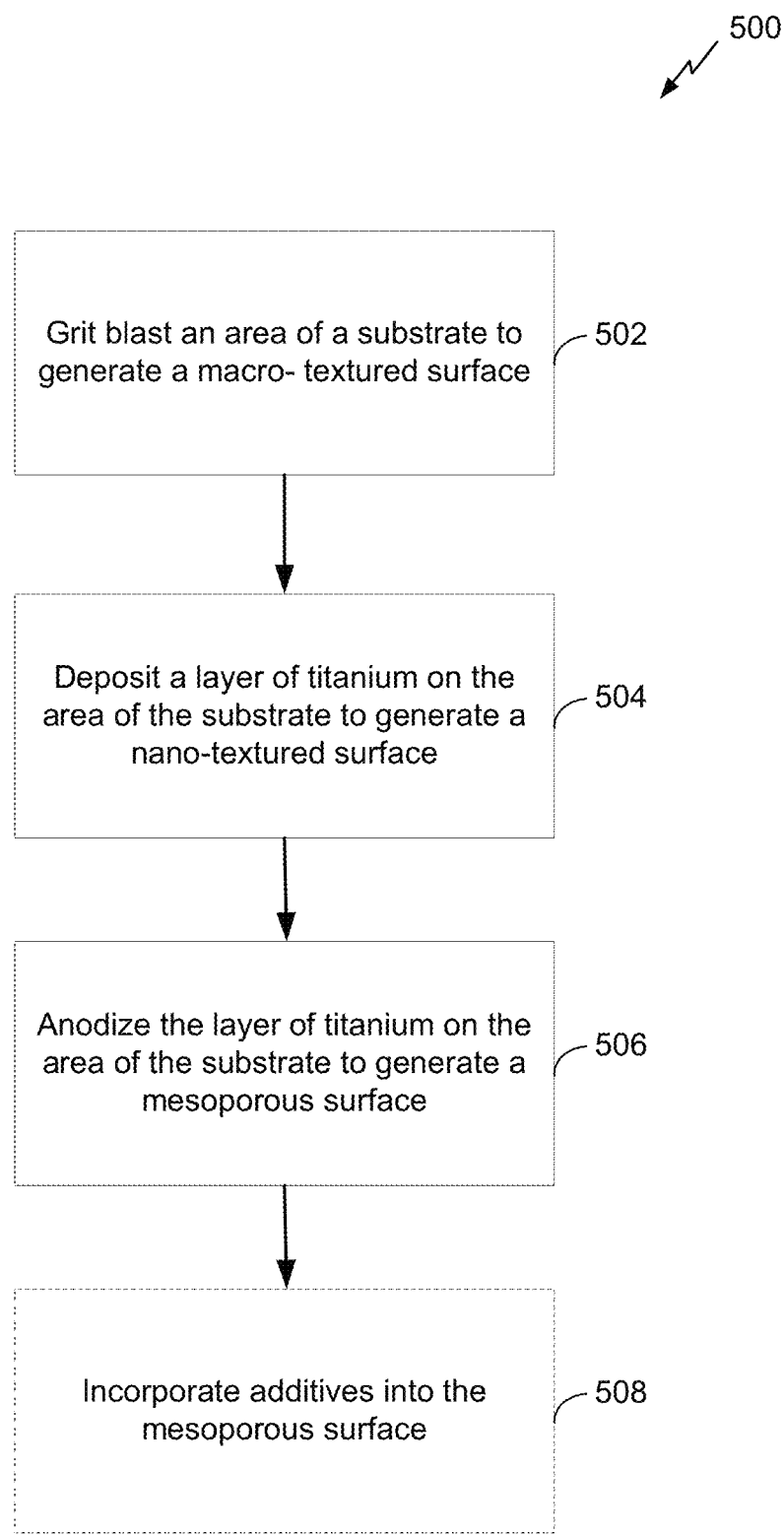
FIG. 5 is a process flow diagram for a method of generating a mesoporous surface on a PEEK substrate.

Referring to FIG. 5, with further reference to FIGS. 3, 4A-4C, a method 500 of generating a mesoporous surface on a non-conductive substrate includes the stages shown. The method 500 is, however, an example only and not limiting. The method 500 can be altered, e.g., by having stages added, removed, rearranged, combined, performed concurrently, and/or having single stages split into multiple stages. For example, stage 508 is optional and may not be included in the mesoporous surface.

At stage 502, the method includes grit blasting an area of a substrate to generate a macro textured surface. As an example, and not a limitation, the substrate may be a polyetheretherketone (PEEK) material. The substrate may be a medical device and the method 500 is performed on the medical device to improve osteoblast formation and enhance osseointegration when the medical device is implanted into a living body. In an example, an abrasive grit/air-blasting equipment (e.g., Comco MicroBlaster) may be used to air-blast micro-beads of $SiO_2$, $Al_2O_3$, or other media (e.g., 50-100 μm in diameter) onto the surface of the substrate. The air-blasting may be performed at room temperature and will result in a macro textured surface, such as the PEEK substrate depicted in FIG. 4A. The processes is not limited to PEEK substrates and may be used to create mesoporous surfaces on other polymers and metals, such as substrates composed at least in part of a thermoplastic, a stainless steel alloy, titanium, cobalt chromium, a ceramic (e.g., alumina, zirconia, aluminum oxynitride, titania, etc.), and/or combinations thereof.

At stage 504, the method includes depositing a layer of titanium on the area of the substrate to generate a nano-textured surface. A layer of Titanium 0.5-10 μm thick, and preferably 2-4 μm thick, may be deposited using the IBAD process onto the grit-blasted area of the substrate. In an example, the system 300 may be used to perform the IBAD process. The system 300 utilizes a line-of-sight process and the substrate may be attached to the substrate holder 360 during processing to help ensure that all surfaces of the area on the substrate are evenly coated. The IBAD process parameters will be chosen so as to produce highly-adherent micro- and nano-textured Ti layers on substrates similar to those shown in FIG. 4B. For example, the IBAD process may include evaporant deposition rates between about 0.5 Angstroms per second (Å/s) to approximately 100 Å/s, and preferably from about 5 Å/s to approximately 30 Å/s. The arrival rate of the ion beam can be in a range between about 10 to about 500 microamperes per square centimeter per second ($\mu A/cm^2/sec$). The ion beam energy may be 50 electron volts (eV) to about 5000 eV. The backfill species may be one or more reactive gases, for example, oxygen and/or nitrogen. The backfill flow rate may be ≤100 SCCM.

At stage 506, the method includes anodizing the layer of titanium on the area of the substrate to generate a mesoporous surface. In an example, an electrochemical oxidation process (e.g. Anodization) in a hydrofluoric (HF) acid-based solution may be used to produce mesoporous $TiO_2$ structure within the Ti coating nano-clusters such as depicted in FIG. 4C. Other etchant solutions including ammonium fluoride, nitric acid, hydrochloric acid, acetic acid, tri-chloroacetic acid, phosphoric acid, sulfuric acid, potassium hydroxide, sodium hydroxide or combinations thereof may be used. The anodization process may produce mesoporous $TiO_2$ coatings of various thicknesses, which in turn may produce a full array of interference colors. Variations in appearance colors can potentially be used for product differentiation and as a quality control tool to ensure a device appropriate textured structure is achieved. As an example, and not a limitation, the target thickness of the mesoporous $TiO_2$ layer is about 100-1000 angstroms and may produce pores sizes of approximately 1-50 nanometers across (i.e., lateral dimension) and 10-500 nm in depth. Other thickness and pore sizes may be used based on the application, but in general, the mesoporous layer does not need to be very thick to provide favorable biological response.

At stage 508, the method optionally includes incorporating of pharmaceutical, biological, or molecular additives into the mesoporous structure intended to further enhance performance of the coated implant, for instance via enhanced osseoconduction, osseoinduction, or antimicrobial/anti-infective properties. Such additives can include but are not limited to elements, molecules, fluids, antimicrobials, antibiotics, anti-inflammatories, amino acids, proteins, enzymes, peptides, peptide aptamers, anti-quorum-sensing agents, bacteriophages, or other synthetic or natural compounds derived from plants and other microbes.

Other examples and implementations are within the scope and spirit of the disclosure and appended claims. For example, due to the nature of software and computers, functions described above can be implemented using software executed by a processor, hardware, firmware, hardwiring, or a combination of any of these. Features implementing functions may also be physically located at various positions, including being distributed such that portions of functions are implemented at different physical locations.

Also, as used herein, "or" as used in a list of items prefaced by "at least one of" or prefaced by "one or more of" indicates a disjunctive list such that, for example, a list of "at least one of A, B, or C," or a list of "one or more of A, B, or C" means A or B or C or AB or AC or BC or ABC (i.e., A and B and C), or combinations with more than one feature (e.g., AA, AAB, ABBC, etc.).

As used herein, unless otherwise stated, a statement that a function or operation is "based on" an item or condition means that the function or operation is based on the stated item or condition and may be based on one or more items and/or conditions in addition to the stated item or condition.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed to control the grit-blasting, IBAD process, and/or anodization processes.

The terms "machine-readable medium" and "computer-readable medium," as used herein, refer to any medium that participates in providing data that causes a machine to operate in a specific fashion. Using a computer system, various computer-readable media might be involved in providing instructions/code to processor(s) for execution and/or might be used to store and/or carry such instructions/code (e.g., as signals). In many implementations, a computer-readable medium is a physical and/or tangible storage medium. Such a medium may take many forms, including but not limited to, non-volatile media and volatile media. Non-volatile media include, for example, optical and/or magnetic disks. Volatile media include, without limitation, dynamic memory.

Common forms of physical and/or tangible computer-readable media include, for example, a floppy disk, a flexible disk, hard disk, magnetic tape, or any other magnetic medium, a CD-ROM, any other optical medium, punchcards, papertape, any other physical medium with patterns of holes, a RAM, a PROM, EPROM, a FLASH-EPROM, any other memory chip or cartridge, a carrier wave as described hereinafter, or any other medium from which a computer can read instructions and/or code.

Various forms of computer-readable media may be involved in carrying one or more sequences of one or more instructions to one or more processors for execution. Merely by way of example, the instructions may initially be carried on a magnetic disk and/or optical disc of a remote computer. A remote computer might load the instructions into its dynamic memory and send the instructions as signals over a transmission medium to be received and/or executed by a computer system.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Components, functional or otherwise, shown in the figures and/or discussed herein as being connected or communicating with each other are communicatively coupled. That is, they may be directly or indirectly connected to enable communication between them.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of operations may be undertaken before, during, or after the above elements are considered. Accordingly, the above description does not bound the scope of the claims.

Further, more than one invention may be disclosed.

The invention claimed is:

1. A method for generating a mesoporous surface on a substrate, comprising:
    grit-blasting an area of the substrate to generate a macro-textured surface;
    depositing a layer of titanium on the area of the substrate to generate a nano-textured surface; and
    anodizing the layer of titanium on the area of the substrate to generate the mesoporous surface.

2. The method of claim 1 wherein the substrate comprises a polyetheretherketone (PEEK) material.

3. The method of claim 1 wherein grit-blasting the area of the substrate includes air-blasting the area with 50-100 μm in diameter micro-beads of $SiO_2$ or $Al_2O_3$.

4. The method of claim 1 further comprising incorporating pharmaceutical, biological, or molecular additives into the mesoporous surface intended to further enhance performance of the substrate via enhanced osseoconduction, osseoinduction, or antimicrobial/anti-infective properties.

5. The method of claim 1 comprising depositing the layer of titanium on the area of the substrate with an ion beam assisted deposition (IBAD) process.

6. The method of claim 5 wherein the IBAD process utilizes an ion beam energy between 50 eV and 5000 eV.

7. The method of claim 1 wherein the layer of titanium is between 0.5 μm to 10 μm thick.

8. The method of claim 1 wherein anodizing the layer of titanium on the area of the substrate includes an electrochemical oxidation process in a hydrofluoric (HF) acid-based solution.

9. The method of claim 1 wherein anodizing the layer of titanium on the area of the substrate includes an electrochemical oxidation process in an ammonium fluoride ($NH_4F$) acid-based solution.

10. The method of claim 1 wherein anodizing the layer of titanium on the area of the substrate includes an electrochemical oxidation process in a solution of nitric acid, hydrochloric acid, acetic acid, trichloroacetic acid, phosphoric acid, sulfuric acid, potassium hydroxide, sodium hydroxide, or combinations thereof.

11. The method of claim 1 wherein the mesoporous surface comprises pore sizes of between 1-50 nanometers in a lateral dimension and between 10-500 nanometers in depth.

* * * * *